(12) United States Patent
Takahashi (10) Patent No.: US 7,033,316 B2
(45) Date of Patent: *Apr. 25, 2006

(54) ENDOSCOPE SYSTEM

(75) Inventor: Tadashi Takahashi, Saitama-ken (JP)

(73) Assignee: PENTAX Corporation, Tokyo (JP)

( * ) Notice: Subject to any disclaimer, the term of this patent is extended or adjusted under 35 U.S.C. 154(b) by 309 days.

This patent is subject to a terminal disclaimer.

(21) Appl. No.: 10/188,096

(22) Filed: Jul. 3, 2002

(65) Prior Publication Data
US 2003/0009083 A1    Jan. 9, 2003

(30) Foreign Application Priority Data

Jul. 6, 2001 (JP) .............................. 2001-206644
Aug. 31, 2001 (JP) .............................. 2001-263445

(51) Int. Cl.
*A61B 1/04* (2006.01)

(52) U.S. Cl. .................. 600/118; 600/109; 348/72; 348/74

(58) Field of Classification Search ................ 600/118, 600/109; 348/65, 72, 74, 76; 707/206; 711/170
See application file for complete search history.

(56) References Cited

U.S. PATENT DOCUMENTS

| | | | | |
|---|---|---|---|---|
| 4,862,872 A | * | 9/1989 | Yabe et al. | 600/133 |
| 4,996,975 A | * | 3/1991 | Nakamura | 600/118 |
| 5,539,904 A | * | 7/1996 | Brauns et al. | 707/2 |
| 5,871,439 A | * | 2/1999 | Takahashi et al. | 600/118 |
| 5,967,969 A | * | 10/1999 | Enomoto et al. | 600/117 |
| 6,256,634 B1 | * | 7/2001 | Moshaiov et al. | 707/100 |
| 6,322,496 B1 | * | 11/2001 | Iida et al. | 600/118 |
| 6,436,032 B1 | * | 8/2002 | Eto et al. | 600/117 |
| 6,609,135 B1 | * | 8/2003 | Omori et al. | 707/104.1 |
| 6,638,212 B1 | * | 10/2003 | Oshima | 600/109 |
| 6,712,756 B1 | * | 3/2004 | Kura et al. | 600/118 |
| 2001/0002842 A1 | * | 6/2001 | Ozawa | 348/45 |

OTHER PUBLICATIONS

U.S. Appl. No. 10/183,429, filed Jun. 28, 2002, Takahaski and entitled "An Endoscope System".

* cited by examiner

*Primary Examiner*—John P. Leubecker
(74) *Attorney, Agent, or Firm*—Greenblum & Bernstein, P.L.C.

(57) ABSTRACT

An endoscope system including a database and a database managing device is disclosed. The database is configured to store a plurality of pieces of endoscope data. Each piece of the endoscope data corresponds to a different endoscope and is associated with ownership information indicating a term for which the corresponding endoscope is allowed to be utilized. The database managing device selects the piece of endoscope data to be replaced based on the ownership information. The ownership information includes information on whether the corresponding endoscope is purchased or not The database managing device selects and replaces the piece of endoscope data related to the endoscope that is not purchased in preference to purchased endoscope data.

12 Claims, 11 Drawing Sheets

| Address | 0 | 3 | 9 | 10 | 11 | 12 | 13 |
|---|---|---|---|---|---|---|---|
| | serial no. (3bytes) | scope name (6bytes) | wb(r) (1byte) | wb(b) (1byte) | owner-ship (1byte) | spec (1byte) | expiration (3bytes) |

FIG. 3

| item | contents |
|---|---|
| serial_no. | 820523(0×0c852b) |
| scope_name | "FG−26D"(0×46472d3233644) |
| wb(r) | −4(0×7c) |
| wb(b) | +10(0×8a) |
| ownership | 1(0×1) |
| spec | 1(0×1) |
| expiration | 040331(0×040031f) |

| register no. | scope name | serial no. | white balance | | owner-ship | spec | expiration | registered date & time | used date & time | count |
| --- | --- | --- | --- | --- | --- | --- | --- | --- | --- | --- |
| | | | wb(r) | wb(b) | | | | | | |
| 1 | FG-28A | 525813 | +4 | +5 | 0 | 0 | 0 | 971213.1313 | 001016.0913 | 159 |
| 2 | FC-34B | 631426 | +16 | +12 | 0 | 0 | 0 | 971213.1326 | 001014.1039 | 283 |
| 3 | FS-34A | 856339 | +1 | −9 | 1 | 0 | 010531 | 971213.1339 | 991230.1513 | 229 |
| 4 | FC-27A | 297813 | −3 | +3 | 0 | 1 | 0 | 001015.0924 | 001016.1712 | 3 |
| 5 | FD-32A | 646526 | 0 | +2 | 1 | 0 | 030331 | 971213.1413 | 000908.0839 | 145 |
| ... | ... | ... | ... | ... | ... | ... | ... | ... | ... | ... |
| 38 | FG-21A | 790526 | +10 | +6 | 0 | 0 | 0 | 000913.0826 | 001018.1113 | 13 |
| 39 | FC-29A | 693639 | −2 | −5 | 2 | 0 | 001019 | 001018.0839 | 001018.1426 | 26 |

ENDOSCOPE SYSTEM

BACKGROUND OF THE INVENTION

The present invention relates to an endoscope system adapted to manage data of a plurality of endoscopes.

There are endoscopes provided with a solid state imaging device for capturing images inside a human body. Such endoscopes, so called electronic endoscopes, are normally connected to a processor that transforms the output signals from the solid state imaging device into image signals so that output devices such as monitors and video printers can display or print the image captured by the solid state imaging device.

The endoscope is connected detachably to the processor so that the endoscope can be changed to a suitable type in accordance with the location of the human body to be inspected or treated with the endoscope. That is, the endoscope and the processor can be used in various combinations.

The endoscope is usually provided with a memory, such as an EEPROM, into which various kinds of data related to the endoscope are stored. Data stored into the memory includes, for example, type and serial number of the endoscope, and calibration data for adjusting the white balance of the image captured by the solid state imaging device. The calibration data for adjusting the white balance includes the amount of brightness increase/decrease of red and blue colors, which will be referred hereinafter as "wb(r)" and "wb(b)", respectively.

The endoscope type and serial number are read by the processor as the endoscope is connected, and displayed on, for example, a monitor. An operator can check the information about the endoscope from the serial number by searching a database, for example, constructed in an independent computer. There is, however, information which should be checked whenever the endoscope is used. Such information requires repetitive search work which burdens the operator.

Therefore, there is a need for an endoscope system that allows the operator to check information about the endoscope in use in a simpler manner.

The calibration data for white balance, wb(r) and wb(b), is also read by the processor to adjust the white balance of the image generated in the processor based on the output signals from the solid state imaging device.

The color balance adjusting abilities, however, are slightly different between each processor. Therefore, the processor often fails to achieve proper white balance by adjusting the colors in accordance with the calibration data obtained from the endoscope. In such case, proper white balance is achieved by performing manually a fine adjustment.

Recently, processors have been developed that are provided with a memory for storing the calibration data obtained as a result of the fine adjustment mentioned above. The calibration data is stored in the memory in association with data intrinsic to the endoscope, such as serial number, to construct a database. The processor can utilize the calibration data in the database whenever the endoscope is connected and used again in the future. In this way, the processor eliminates the necessity of repetitive manual fine adjustment of the white balance.

The number of endoscopes, however, of which data can be registered to the database is restricted because of the finite available memory space thereof. Thus, if there is not available memory space for storing data of a new endoscope, unimportant data such as that of old or seldom used endoscopes should be deleted manually to free up memory space. Such manual operation is a cumbersome task and may cause deletion of important data such as that of new or frequently used endoscopes if proper care is not used when manually deleting data.

Therefore, there is also a need for an endoscope system that manages the database of endoscope data such that the deletion of important data is prevented.

SUMMARY OF THE INVENTION

The present invention provides the advantage in that, in an endoscope system, important data of endoscopes in a database is prevented from being unintentionally deleted. The present invention also provides the advantage that the operator can check information about the endoscope in use in a simple manner.

According to an aspect to the invention, an endoscope system including a database and a database managing device is provided. The database is configured to store a plurality of pieces of endoscope data. Each piece of the endoscope data corresponds to a different endoscope and is associated with ownership information indicating a term for which the corresponding endoscope is allowed to be utilized. The database managing device is configured to select one of the plurality of pieces of endoscope data stored in the database and replace it with a new piece of endoscope data corresponding to a new endoscope. The database managing device selects the piece of endoscope data to be replaced based on the ownership information. In this manner, the database managing device can select and replace the piece of endoscope data of the database so that, for example, the endoscope data that corresponds to the endoscopes allowed to be utilized for relatively long term remains in the database.

The ownership information may include information on whether the corresponding endoscope is purchased or not. Purchased endoscopes are generally allowed to be used permanently and therefore the piece of endoscope data corresponding to purchased endoscopes should be left in the database. Accordingly, the database managing device may select and replace the piece of endoscope data related to the endoscope that is not purchased in preference to purchased endoscope data.

Alternatively, the ownership information may include information on whether the corresponding endoscope is leased or not. Since the leased endoscope is allowed to be utilized for only a limited term, the database managing device may select the piece of endoscope data related to the endoscope being leased in preference to other endoscope data and replace it with the new endoscope data.

In addition, the ownership information may include information on whether a term of lease of the endoscope is less than a predetermined period in this case, the database managing device may select the piece of endoscope data related to the term of lease less than the predetermined period in preference to other endoscope data. Alternatively, the database managing device may select the piece of endoscope data related to the term of lease which has already expired since such endoscope may not be utilized in the future again.

Optionally, each of the pieces of the endoscope data is associated with registration information including a date of when the piece of endoscope data is stored into the database, and the database managing device selects one piece of the endoscope data to be replaced based on the registration information among a plurality of pieces of the endoscope data selected based on the ownership information. In particular, the database managing device may select the piece of endoscope data related to the registration information including the oldest date since such old endoscope data may have less importance than those registered later.

Alternatively, each of said pieces of endoscope data is associated with used date information including a date of the corresponding endoscope being used for the last time. The database managing device selects one piece of the endoscope data to be replaced based on the used date information among a plurality of pieces of the endoscope data selected based on said ownership information. In particular, the database managing device may select the endoscope data related to the used data information including the oldest date, since the endoscope not used for a long time may be seldom used also in the future.

Optionally, the database and the database managing device are provided to a processor configured to be connected to the endoscope for receiving and processing signals from the endoscope.

According to another aspect to the invention, an endoscope system including a processor and an output device is provided. The processor is connectable to various endoscopes to receive and process signals from the endoscopes being connected. The processor includes a database configured to store a plurality of pieces of endoscope data each corresponding to a different one of said endoscopes. Each piece of the endoscope data is associated with ownership information which indicates a term for which the corresponding endoscope is allowed to be utilized. The output device is configured to output the ownership information so that an operator of the endoscope system can confirm the ownership information.

Optionally, the output device outputs the ownership information of the endoscope currently connected to the processor so that the operator can confirm the ownership information of the endoscope currently connected.

Optionally, the output device is a monitor for displaying an image captured by an imaging device provided to the endoscope. In this case, the ownership information can be displayed, for example, simultaneously with the image captured by the imaging device.

According to another aspect of the invention, specifications information, indicating the design specifications of the corresponding endoscope, is associated with each piece of the endoscope data in the database instead of the ownership information and outputted from the output device so that the operator can confirm the specifications of the endoscope.

According to another aspect of the invention, an endoscope system including a database and a database managing device is provided. The database is configured to store a plurality of pieces of endoscope data each corresponding to a different endoscope. Each piece of the endoscope data is associated with term information which indicates a term the corresponding piece of endoscope data is valid. In order to prevent the database from being filled with invalid endoscope data, the database managing device is configured to selectively delete the piece of endoscope data in the database based on the term information.

According to another aspect of the invention, an endoscope including a storage device configured to store ownership information and/or specifications information is provided. The ownership information includes a term for which the endoscope is allowed to be utilized, while the specifications information indicates design specifications of the endoscope.

DETAILED DESCRIPTION OF THE EMBODIMENTS

Hereinafter, embodiments of the invention will be described with reference to the accompanying drawings.

Figure 1:
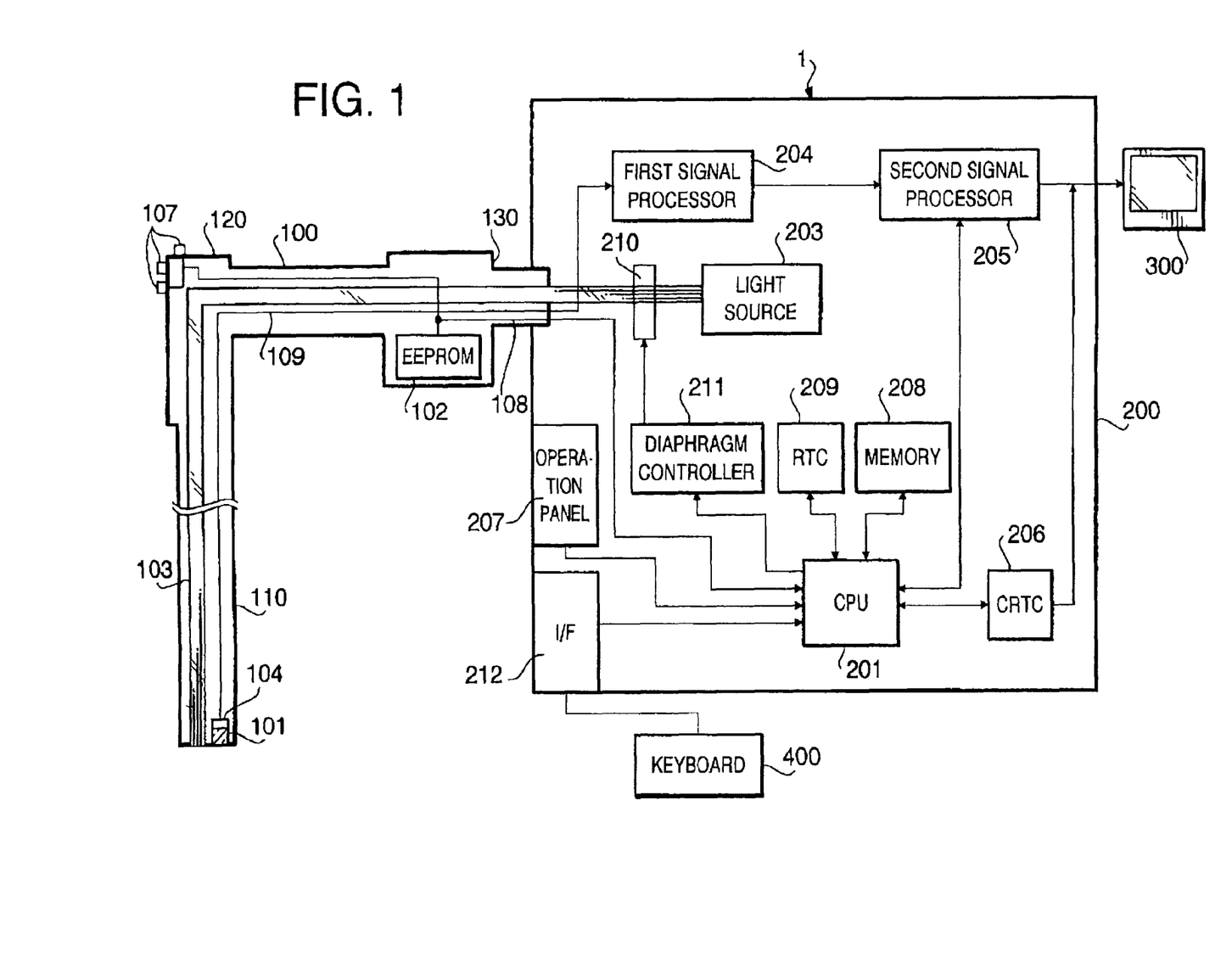
FIG. 1 schematically shows the configuration of an electronic endoscope system according to an embodiment of the invention.

FIG. 1 schematically shows the configuration of an electronic endoscope system 1 according to an embodiment of the invention.

The electronic endoscope system 1 includes an electronic endoscope 100 and a processor 200 for processing signals from the electronic endoscope 100.

The electronic endoscope 100 includes an flexible inserting tube 110 to be inserted into a human body and an operation portion 120 connected to the proximal end of the inserting tube 110. The electronic endoscope 100 further includes a connector 130 which is detachably connected to the processor 200.

A solid state imaging device such as a CCD 104 and an objective optical system 101 for forming an optical image on a light receiving surface of the CCD 104 are provided to the distal end portion of the inserting tube 110.

Further, one or more operation buttons 107 are provided to the operation portion 120 for controlling the operation of the processor 200.

Further, a memory such as an EEPROM 102 is provided to the electronic endoscope 100 for storing data related to the endoscope 100, in particular, data intrinsic to each endoscope. In the present embodiment, the EEPROM 102 is located in the connector 130.

The processor 200 includes a CPU 201 which is connected to the operation buttons 107 and the EEPROM 102 via an signal cable 108. The CPU 210 controls the operation of the processor 200 in accordance with the signals from the operation buttons 107. The CPU 210 also accesses the EEPROM 102 to retrieve data stored therein.

The CPU 201 is further connected to an input unit, such as a keyboard 400, via an interface 212, to control the operation of the processor 200 in accordance with the commands inputted from the keyboard 400.

The processor 200 is also provided with an operation panel 207. A plurality of operation buttons (not shown) are arranged on the operation panel 207 such that an operator of the endoscope system 1 can press each button. Each button outputs a signal to the CPU 201, as being pressed, to control the operation of the processor 200.

The processor includes a light source 203 optically connected to the end of a light guide 103 that is arranged throughout the electronic endoscope 100 from the connector 130 to the tip end of the inserting tube 110. The light emitted from the light source 203 is transmitted through the light guide 103 to illuminate the area in front of the tip end of the inserting tube 110.

An diaphragm 210 is provided on the light path of the light emitted from the light source 203 to restrict the amount of light introduced into the light guide 103. An diaphragm controller 211 controls the opening size of the diaphragm 210, or the amount of light introduced into the light guide 103, in accordance with signals from the CPU 201. The operator can freely control the opening size of the diaphragm 210 by operating the keyboard 400 or the operation panel 207.

First and second signal processors 204 and 205 are provided to the processor 200 to display images captured by the CCD 104 on a monitor 300. The first signal processor 204 receives the signal from the CCD 104 via a CCD signal cable 109 and transforms it into RGB digital image data represented in 256 levels of gray scale. The first signal processor 204 outputs the digital image data to the second signal processor 205 which generates video signal, such as NTSC, from the digital image data. The second signal processor 205 further adjusts the white balance of the video signal based on calibration data wb(r) and wb(b) received from the CPU 201 as will be described later. The second signal processor 205 outputs the video signal to the monitor 300 so that the monitor 300 displays the image captured by the CCD 104.

Note that the output device to which the second signal processor 205 may be connected is not limited to the monitor 300, however, the second signal processor 205 may also be connected to other kinds of output devices such as a video printer, for example.

A CRT controller 206 is provided to the processor to superimpose text information on the image displayed on the monitor 300. The CRT controller 206 generates video signals representing the text information requested by the CPU 201 and output the video signals to the monitor 300 in synchronization with the video signal from the second signal processor 205. In this way, the processor 200 superimposes arbitrary text information, such as information obtained from the CPU 201, on the image captured by the CCD 104.

The processor 200 is also provided with a Real Time Clock (RTC) 209 and a memory 208. The RTC 209 provides information on current date & time to the CPU 201. The memory 208 is adapted to include a database for data related to endoscopes, as will be described later.

Figure 2:
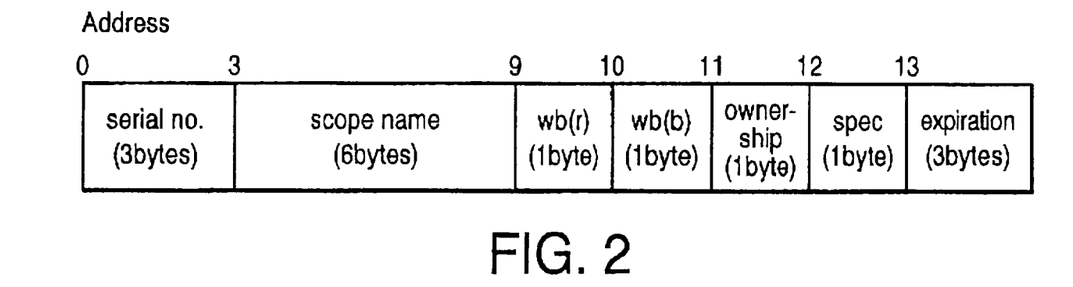
FIG. 2 shows an exemplary data format of a memory provided to an electronic endoscope in the electronic endoscope system of FIG. 1.
Figure 3:
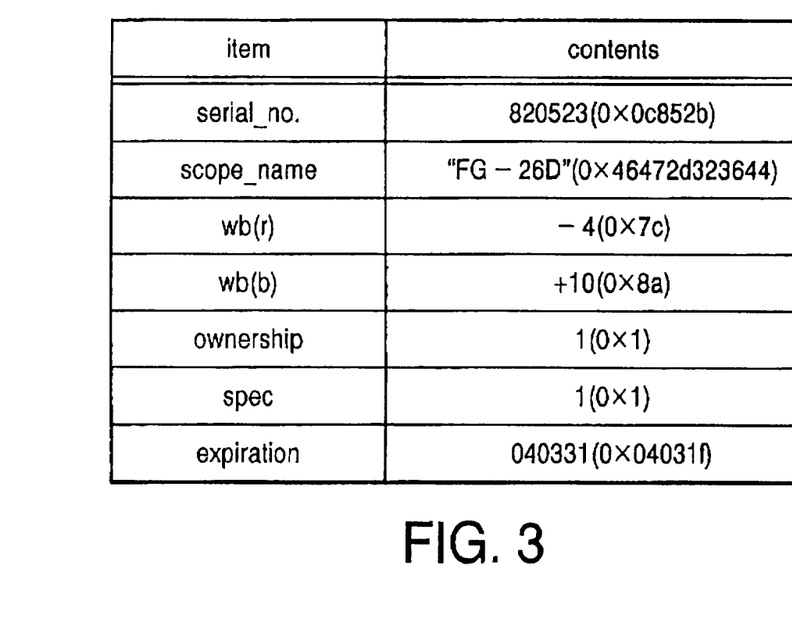
FIG. 3 shows an example of the data stored in the memory of the electronic endoscope in FIG. 1.

FIG. 2 shows an exemplary data format of the EEPROM 102, and FIG. 3 shows an example of the data stored in the EEPROM 102.

In the present embodiment, the storage capacity of the EEPROM 102 is 16 bytes and the following information are stored in the EEPROM 102 in the following order.

1) "serial no." (three bytes): the serial number of the electronic endoscope 100 which is unique for each endoscope. The "serial no." may be set to one of values from 1 through 16777215 (0×1 through 0×ffffff in hexadecimal digit).

2) "scope name" (six bytes): six alphanumeric characters representing the type of the electronic endoscope 100.

3) "wb(r)" (one byte): a calibration value of the red color brightness for adjusting white balance of the image captured by the CCD 104.

4) "wb(b)" (one byte): a calibration value of the blue color brightness for adjusting white balance of the image captured by the CCD 104 Both "wb(r)" and "wb(b)" can take a value between −128 and 127. As shown in FIG. 3, "wb(r)" and "wb(b)" are respectively set to −4 and 10 (0×7 c and 0×8 a in hexadecimal digit) in the present embodiment. This indicates the brightness of red color should be decreased by four levels in gray scale, while the brightness of blue should be increased by ten levels.

5) "ownership" (one byte): a variable representing whether the endoscope is purchased or leased. "ownership"=0, 1 and 2 (0×0, 0×1, and 0×2 in hexadecimal digit) respectively represents whether the endoscope is purchased, leased for a long term (a term not less than 30 days, for example), or leased for a short term (term less than 30 days, for example).

6) "spec" (one byte): a variable representing the specifications of the design of the electronic endoscope 100. If the electronic endoscope 100 is a standard type, then "spec" is set to 0. If the electronic endoscope is a custom made one, then "spec" is set to a value corresponding to the particular design specifications. In the present embodiment, "spec" is set to 1 which indicates the optical system 101 includes a lens applied with special coatings.

7) "expiration" (three bytes): the expiration date of the lease of the electronic endoscope 100. The first one byte of "expiration" indicates the year, the next one the month, and the last one the day. In the example shown in FIG. 3, value 040331 is assigned to "expiration" which indicates the expiration of the lease is Mar. 31, 2004. If the electronic endoscope 100 is a purchased one, then 000000 is assigned to "expiration". It should be noted that, in some embodiments of the invention, "expiration" indicates the expiration date of the service life of the endoscope instead of the expiration date of the lease.

Among the items recited above, the "serial no.", "scope name", "ownership", and "expiration" are examples of information for managing the endoscope, while "wb(r)", "wb(b)", and "spec" are examples of information representing the characteristics of the endoscope.

The data of EEPROM 102 are copied to the memory 208 of the processor 200 as the electronic endoscope 100 is connected to the processor 200 for the first time to register the endoscope to the database.

Figure 4:
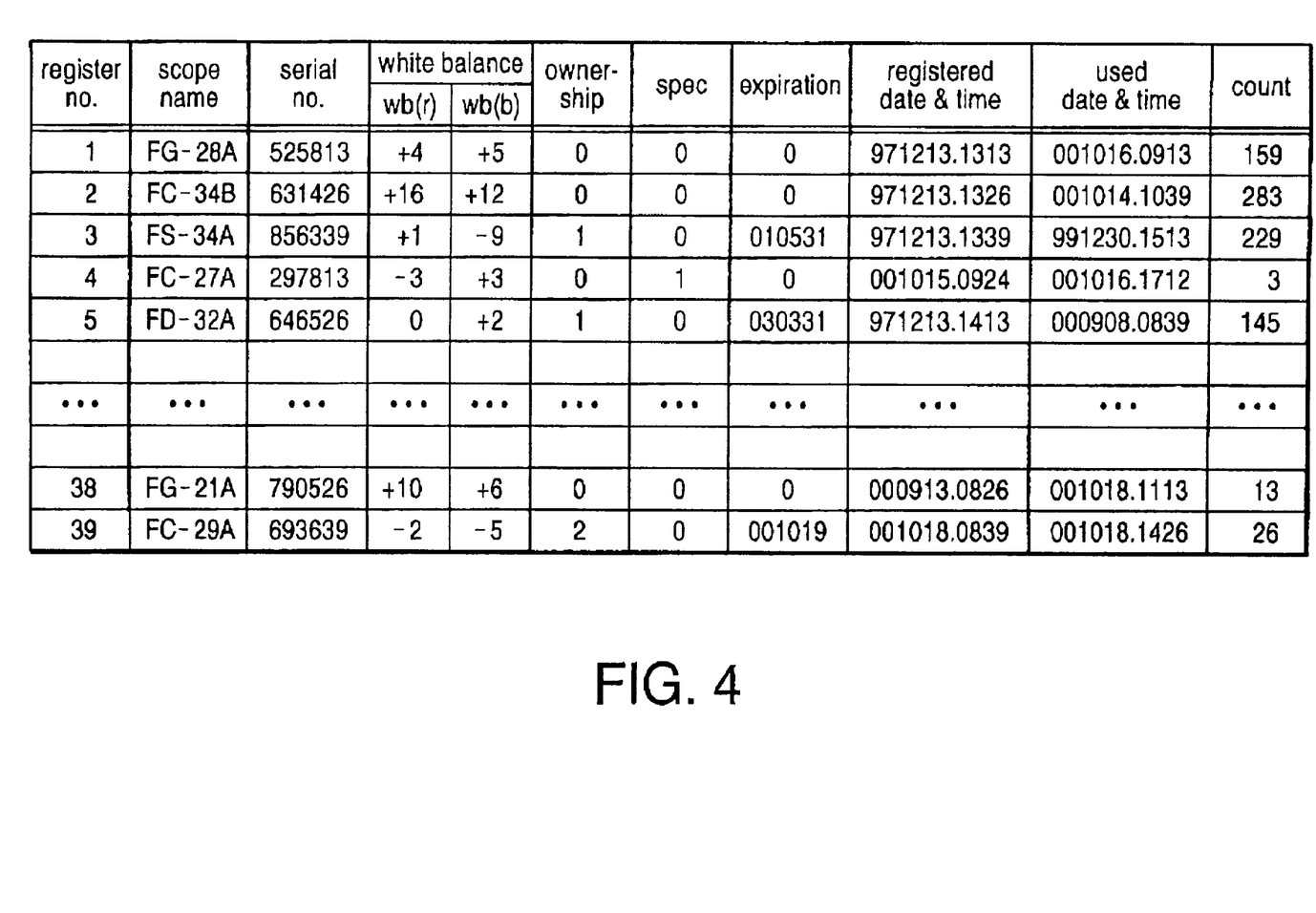
FIG. 4 shows an exemplary structure of a database established in a memory of a processor in the electronic endoscope system of FIG. 1.

FIG. 4 shows an exemplary structure of the database established in the memory 208 of the processor 200. The database includes 39 records, each record being defined for storing data related to one specific endoscope. Thus, data of 39 endoscopes can be stored in the database.

Each record includes the following items in the following order,
1) "register no.",
2) "scope name"
3) "serial no.",
4) "wb(r)",
5) "wb(b)",
6) "ownership
7) "spec",
8) "expiration",
9) "registered date & time",
10) "used date & time",
11) "count".

"register no." is utilized for identifying the record. In the present embodiment, a serial number from 1 to 39 is assigned to the records.

"scope name", "serial no.", "wb(r)" and "wb(b)", "ownership", "spec", and "expiration", are items same as that in the EEPROM 102.

"registered date & time" is the date and time when the electronic endoscope 100 is connected to the processor 200 for the first time. "registered date & time" includes six figures date information and four figures time information. If "registered date & time" is set to "021015.1424", for example, then it represents Oct. 15, 2002, 2:24 p.m.

"used date & time" is the date and time when the electronic endoscope 100 was connected to the processor 200, or used, for the last time. The format of "used date & time" is the same as that of "registered date & time".

"count" is the number of times the electronic endoscope 100 is connected to the processor 200, or used. This variable may be used as an indication of the frequency the endoscope is used.

Figure 5:
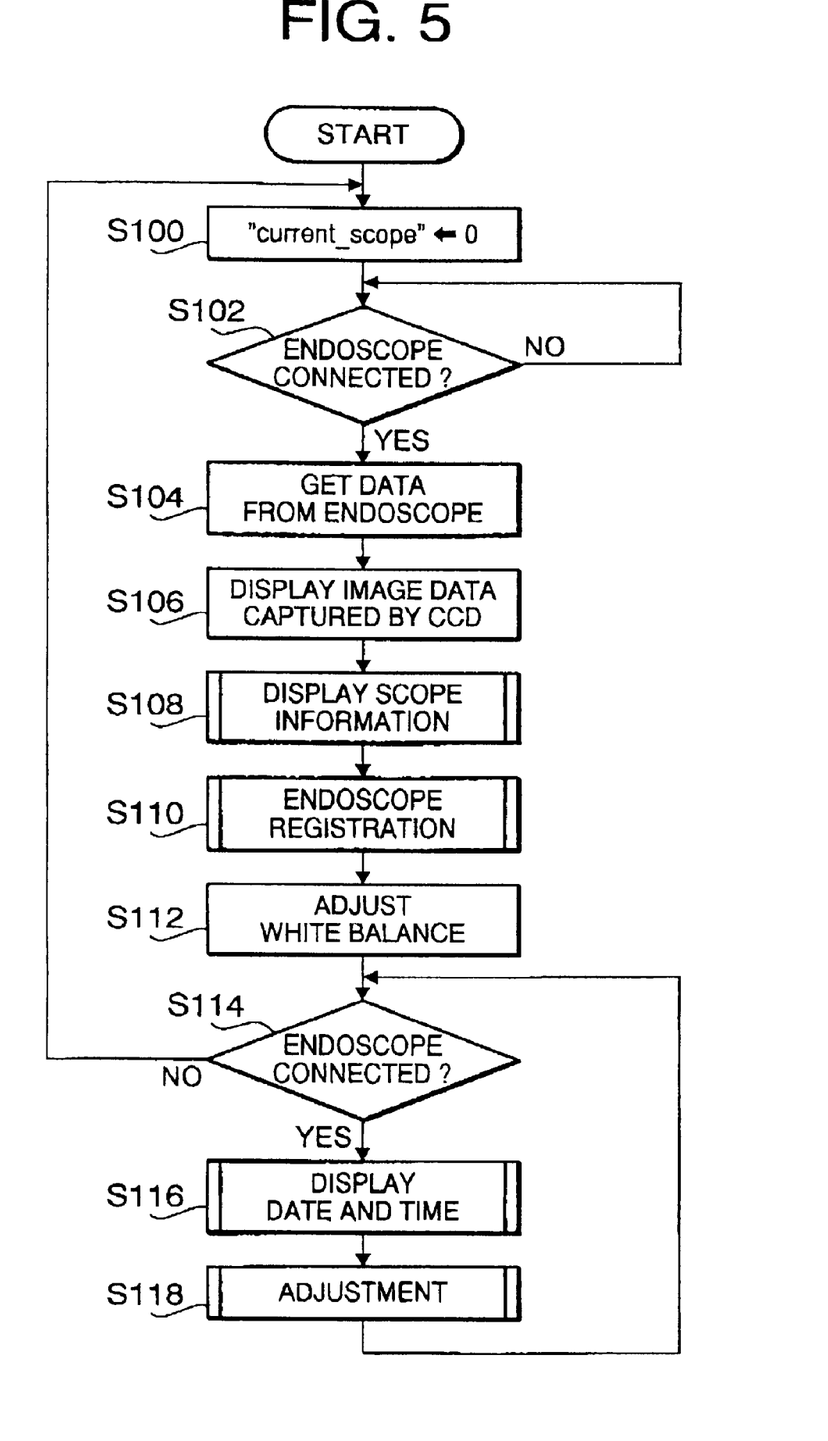
FIG. 5 is a flow chart showing a main routine representing the operation of the processor of the electronic endoscope system shown in FIG. 1 according to an embodiment of the invention.

FIG. 5 is a flow chart showing a main routine of the operation of the processor 200 according to an embodiment of the invention.

At first, the CPU 201 of the processor 200 initializes a variable "current_scope" to 0 (S100). The variable "current_scope" is for storing the "register no." of the record in which the data of the endoscope currently connected to the processor 200 is stored. If 0 is assigned to "current_scope", it represents that no endoscope is currently connected to the processor 200.

After the initialization of "current_scope", the CPU 201 remains in an idle state until the electronic endoscope 100 is connected to the processor 200(S102).

When the electronic endoscope 100 is connected to the processor 200 (S102: Yes), the CPU 201 accesses the EEPROM 102 of the electronic endoscope 100 and obtains the data stored therein (S104). Next, the first and second signal processors 204, 205 transform the output signal from the CCD 104 into video signal to display the image captured by the CCD on the monitor 300 (S166).

Then, the CPU 201 executes a subroutine DISPLAY SCOPE NAME to display the information of the electronic endoscope 100 currently connected to the processor 200 on the monitor 300 (S108). Then, a subroutine ENDOSCOPE REGISTRATION is executed to store the data obtained from the EEPROM 102 into the database established in the memory 208 (S110).

Next, the white balance of the image captured by the CCD 104 of the electronic endoscope 100 is adjusted using the calibration value ("wb(r)", "wb(b)") obtained form the EEPROM 102 (S112) That is, the CPU 201 sends the calibration value of "wb(r)" and "wb(b)" to the second signal processor 205 so that the second signal processor 205 adjusts the color balance of the image signals generated there.

After S112, the processor watches whether the electronic endoscope 100 is still connected, and as long as the electronic endoscope 100 is still connected to the processor 200 (S114:Yes), the processor 200 displays the current date and time on the monitor 300 by executing a subroutine DISPLAY DATE & TIME (S116), and also performs various kinds of adjustments in accordance with manual operation by the operator by executing a subroutine ADJUSTMENT (S118).

If the electronic endoscope 100 is disconnected from the processor 200 (S114:No), the operation of the processor 200 returns to S100.

Figure 6:
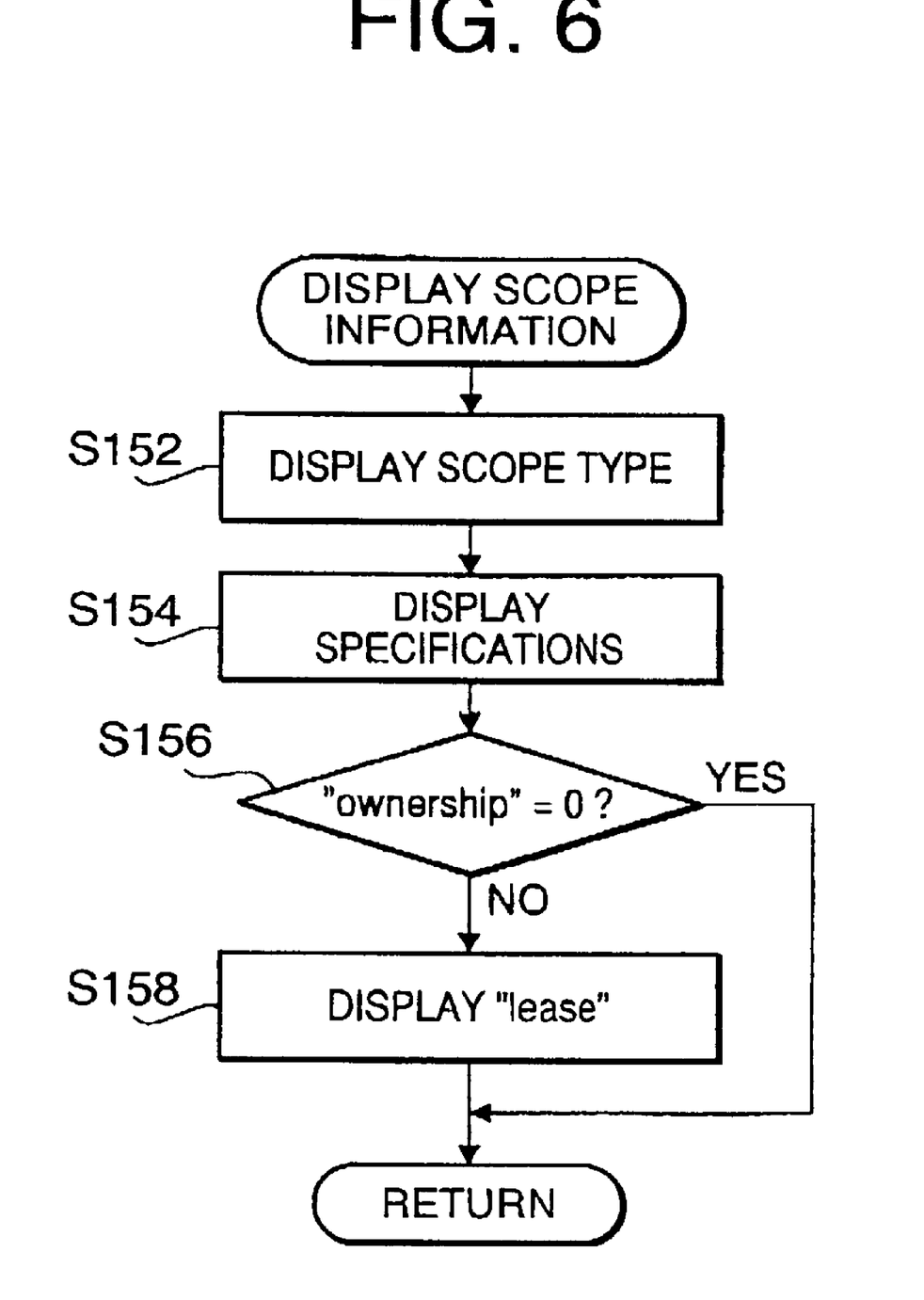
FIG. 6 is a flow chart showing a subroutine DISPLAY SCOPE INFORMATION of the main routine shown in FIG. 5.

FIG. 6 is a flow chart showing the subroutine DISPLAY SCOPE INFORMATION called in S108 of the main routine shown in FIG. 5.

In this routine, the CPU 201 sends the alphanumeric characters of the "scope name" obtained from the EEPROM 102 to the CRT controller 206 to superimpose the type of the electronic endoscope 100 on the image captured by the CCD 104 and displayed on the monitor 205 (S152). The CPU 201 also generates a text information that corresponds to the specifications of the electronic endoscope indicated by "spec" and sends it to the CRT controller 206. Thus, the specifications of the electronic endoscope 100 are also superimposed on the image captured by the CCD 102 (S154) Note that other information obtained from the EEPROM 102 such as serial number and data on white balance may also be superimposed on the image displayed by the monitor 300 instead of or together with the scope type and specifications of the electronic endoscope 100, Next, the CPU 201 decides whether the currently connected endoscope is a purchased one or a leased one This is done by checking the value of "ownership" obtained from the EEPROM 102 (S156).

If "ownership" indicates the endoscope is leased, ie., "ownership"=1 or 2, then the CPU 201 sends a command to the CRT controller 206 to superimpose characters "lease" on the image displayed on the monitor 300. Thus, the operator can notice that the currently used endoscope is a leased one (S158). Note that the date of expiration of the term of lease may also be displayed on the monitor 300.

If "ownership", however, indicates that the endoscope is purchased, i.e., "ownership"=0, then S158 is skipped, and the operation of the processor 200 returns to the main flow shown in FIG. 5.

Figure 7:
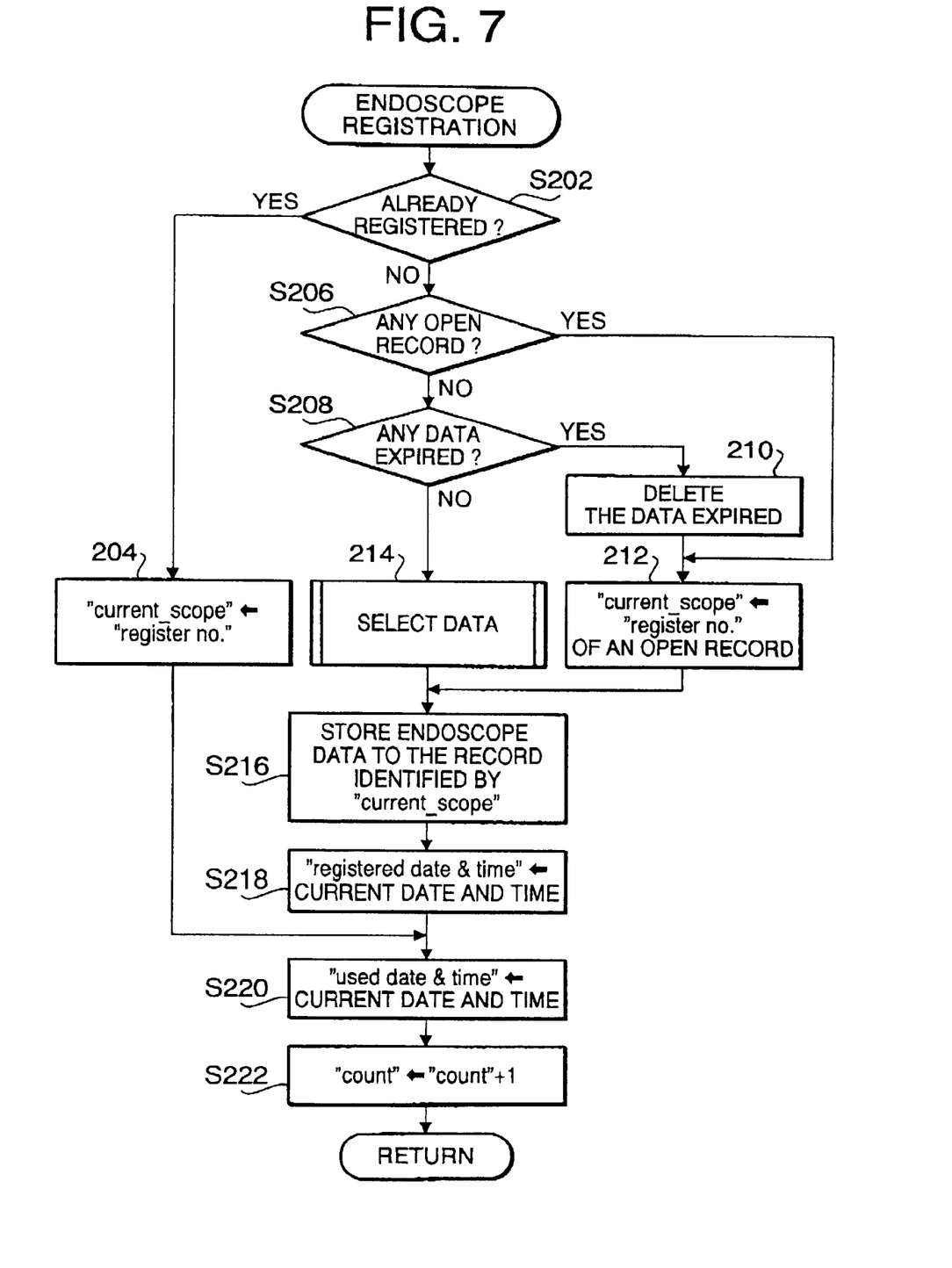
FIG. 7 is a flow chart showing a subroutine ENDOSCOPE REGISTRATION of the main routine in FIG. 5.

FIG. 7 is a flow chart showing the subroutine ENDOSCOPE REGISTRATION called in S110 of the main routine of FIG. 5.

In this routine, the CPU 201 decides whether or not the data related to the currently connected endoscope is already registered with the database in the memory 208 (S202) This is achieved by searching within the memory 208 for a record including data that matches the "scope name" and "serial no." obtained from the EEPROM 102.

If there is a record including the above mentioned data (S202:Yes), it means the data of the electronic endoscope 100 currently connected is already registered in this case, the "register no." of the record found is set to "current_scope" (S204) and the operation of the processor 200 proceeds to S220 which will be described later.

If a record including the above mentioned data is not found (S202:No), it means the electronic endoscope 100 is not yet registered. In this case, the CPU 201 checks whether there is still any available memory space, or open records, within the memory 208 to store the data obtain from the EEPROM 102 (S206).

In the case there is still an open record (S206:Yes), the "register no." of the open record is set to "current scope" (S212). If there are more than one open records, the smallest "register no." is preferably selected and set to the "current scope". After execution of S212, the operation of the processor 200 proceeds to S216 which will be described later.

In the case no open record is found (S206:No), then the CPU 201 checks the term of lease, or "expiration", of each record in the memory 208 (S208). If CPU 201 finds any records of which term of lease has already expired (S208: Yes), then the CPU 201 deletes the data of that record except the register number (S210), since such data are not valid and therefore should not remain in the database. Then, the record deleted at S210 became an open record Further, the CPU 201 sets the register number of the record to "current_scope" (S212).

If there is no record having an expired term of lease (S208:No), then a subroutine SELECT DATA is executed to select one of the records to be freed up for storing the data of the new endoscope (S214). During this subroutine, the register number of the record freed up is set to "current_scope" as will be described later.

After the execution of S212 or S214, the CPU 201 stores the data obtained from EEPROM 102, into the record identified by "current_scope" (S216). Specifically, the CPU 201 stores "serial no.", "scope name", "wb(r)", "wb(b)", "ownership", "spec", and "expiration" obtained from the EEPROM 102 into the record. In this manner, the data of the new endoscope is automatically registered with the database.

It should be noted that instead of data obtained from the EEPROM 102, data manually inputted from the keyboard 400 may be stored into the record specified by "current_scope" so that, for example, data of endoscopes that do not have memories can also be registered to the processor 200.

Next, the CPU 201 obtains the current date and time information from the RTC 209 and stores it in "registered date & time" of the record specified by "current_scope" (S218). This is to make a record of the date and time of registration of the new electronic endoscope 100.

After the execution of S218 or S204, "used date & time" and "count" of the record specified by "current scope" are updated. That is, the current time information obtained from the RTC 209 is overwritten to "used date & time" (S220), and "counts" is incremented by one (S222). After S222, the operation of the processor 200 returns to the main flow shown in FIG. 5.

Figure 8:
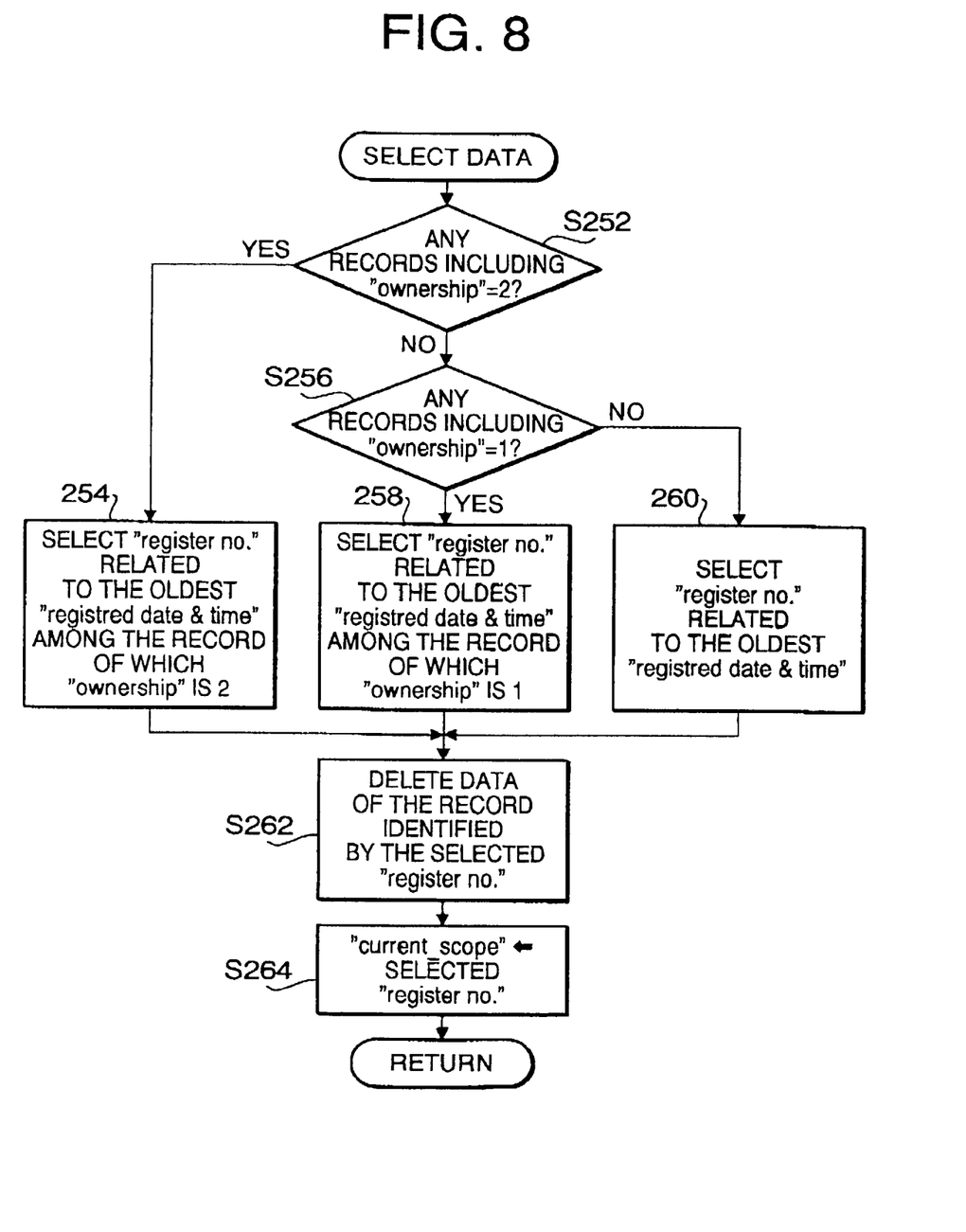
FIG. 8 is a flow chart showing a subroutine SELECT DATA of the subroutine ENDOSCOPE REGISTRATION in FIG. 7.

FIG. 8 is a flow chart showing the subroutine SELECT DATA called in S214 of the subroutine ENDOSCOPE REGISTRATION of FIG. 7. In this subroutine, one record is selected to free up and thereby prepare an open record for storing new data obtained from the currently connected electronic endoscope 100. Records including data of leased endoscopes is selected in preference to other records, and records of endoscopes leased for short terms are selected in further preference to records of endoscopes leased for long terms. Thus, data of endoscopes that the user owns or can keep for a longer time tend to remain in the database.

Specifically, the CPU first checks whether there are any records including data of an endoscope leased for a short term, ie. "ownership"=2 (S252). If there are any (S252:Yes), then the CPU 201 select the record having the oldest "registered date & time" among those records (S254), since the term of lease of such endoscope expires first.

If there isn't any record of which "ownership" is 2 (S252:No), then the CPU 201 searches for records related to endoscopes leased for long terms, i.e., "ownership"=1 (S256). If there are any (S256:Yes), then the CPU 201 selects the record having the oldest "registered date & time" among those records this time also (S258).

If there isn't any record of which "ownership" is 1 (S256:No), i.e., if there isn't any endoscopes leased, then the CPU 201 selects the record having the oldest "registered date & time" among the records including data of purchased endoscope (S260).

After the execution of S254, S258, or S260, the data of the selected record is deleted except "register no." (S262). Further, the "register no." of the selected record is set to "current_scope" (S264). After S264, the operation of the processor 200 returns to the subroutine ENDOSCOPE REGISTRATION shown in FIG. 7.

Figures 9, 10:
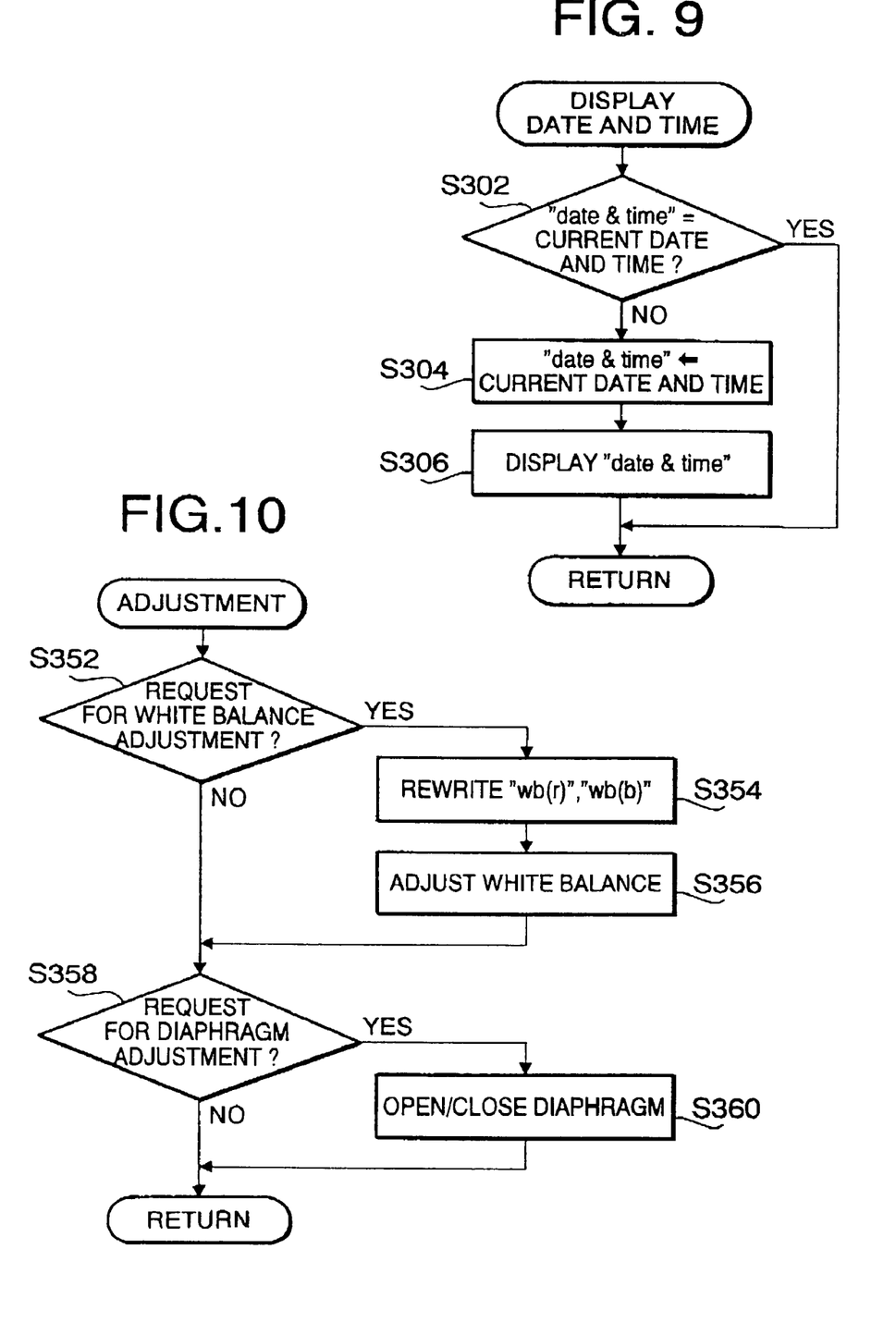
FIG. 9 is a flow chart showing a subroutine DISPLAY DATE & TIME of the main routine shown in FIG. 5.
FIG. 10 is a flow chart showing a subroutine ADJUSTMENT of the main routine shown in FIG. 5.

FIG. 9 is a flow chart showing the subroutine DISPLAY DATE & TIME called in S116 of the main routine shown in FIG. 5.

In this subroutine, the CPU 201 checks whether or not the date and time information of a variable "date & time" indicates the exact time by comparing "date & time" with the date and time information from the RTC 209 (S302).

If the difference between the two pieces of the date and time information is less than a second, then the CPU 201 decides the two pieces of the date and time information are same (S302:Yes). In this case, the operation of the processor 200 immediately returns to the main flow of FIG. 5 without updating the "date & time".

If the difference between the two pieces of date and time information is not less that one second (S302:No), then the date and time information from the RTC 209, or the current date and time, is set to "date & time" (S304). Then, the CPU 201 generates text information indicating the date and time stored in "date & time" such as "May 21, 2002, 15:20:31", for example, and sends it to the CRT controller 206 to superimpose the current date and time on the image displayed by the monitor 300 (S306). In this manner, time information displayed is updated every seconds After the execution of S306, the operation of the processor 200 returns to the main flow shown in FIG. 5.

FIG. 10 is a flow chart showing the subroutine ADJUSTMENT called in S118 of the main routine shown in FIG. 5. This routine is for allowing the operator to manually adjust the white balance of the image captured by the CCD 104, and the opening size of the diaphragm 210.

In this routine, the CPU 201 decides whether or not the adjustment of white balance is requested by checking the signals from the keyboard 400, the operation panel 207, and the operation buttons 107 (S352). If there is a request (S352:Yes), then the CPU 201 rewrites the value of the "wb(r)", "wb(b)" in the record specified by "current scope" in accordance with the signal from the keyboard 400, the operation panel 207, or the operation buttons 107 (S354). Further, the CPU 201 sends the value of latest "wb(r)" and "wb(b)" to the second signal processor 205 so that the second signal processor 205 re-adjusts the white balance of the image generated there (S356).

After the execution of S356 or in the case there isn't any request for white balance adjustment (S352:No), the CPU 201 checks again the output signals from the keyboard 400, the operation panel 207, and the operation buttons 107 to decide whether or not the adjustment of diaphragm size is requested (S358).

If there is a request (S358:Yes), then the CPU 201 opens/closes the diaphragm 210, via the diaphragm controller 211, in accordance with the request from the keyboard 400, the operation panel 207, or the operation buttons 107 to control the amount of light introduced into the light guide 103 (S360).

If the execution of S360 is completed or in the case there isn't any request (S358:No), the operation of the processor returns to the main flow of FIG. 5.

It should be noted that the operation of processor 200 described in FIG. 5 through FIG. 10 may be modified in many ways within the scope of the invention.

Figure 11:
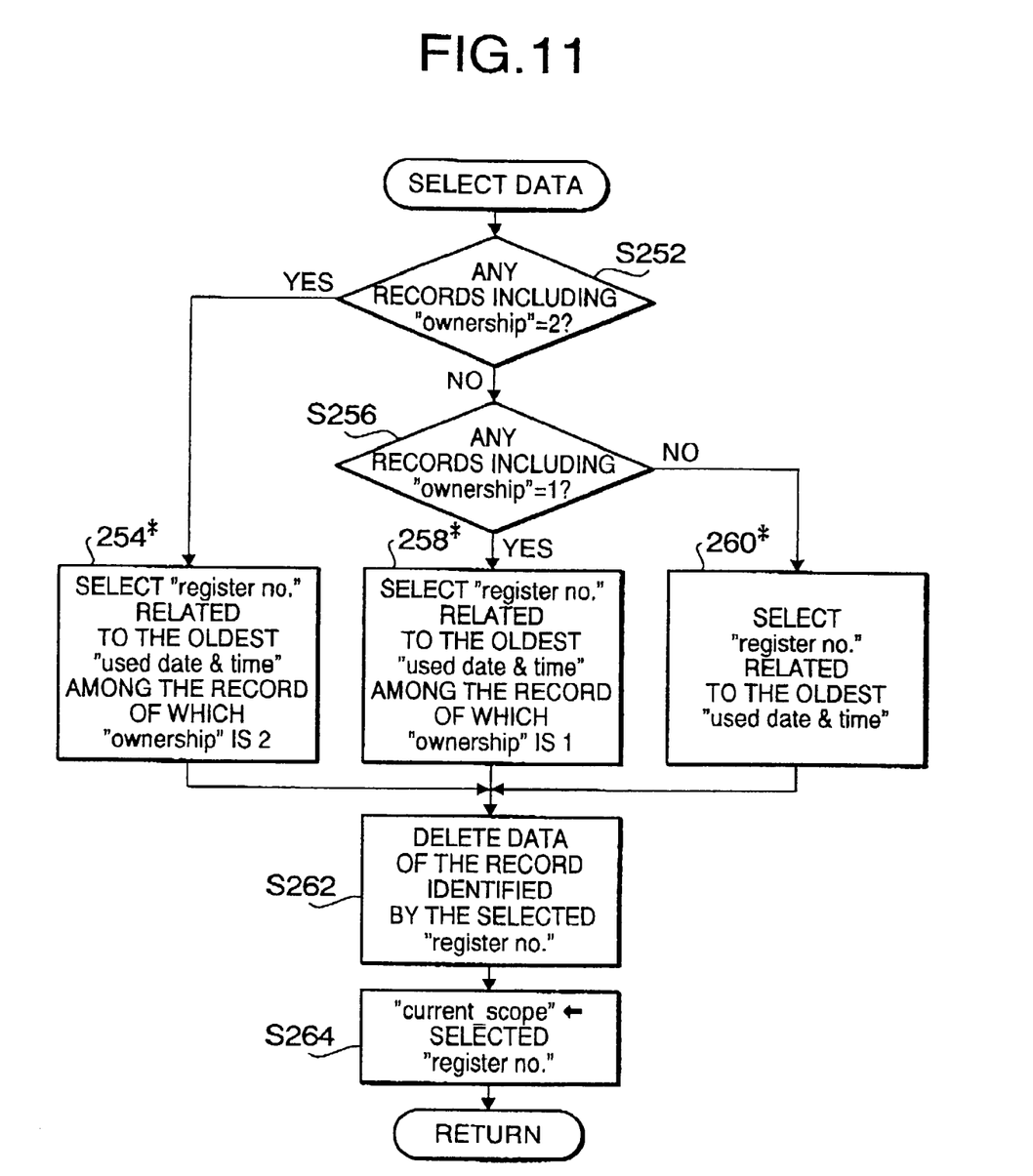
FIG. 11 shows a modification of the subroutine SELECT DATA shown in FIG. 8.

For example, S254, S258, and S260 in the subroutine SELECT DATA shown in FIG. 8 may be replaced with steps that selects the record including the oldest "used date & time" instead of the oldest "registered date & time" as shown in FIG. 11 (see S254*, S258*, and S260*). If S254, S258, and S260 are replaced with S254*, S258*, and S260*, respectively, the data related to the endoscope seldom used, and may have not high possibility to be used again in the future, is deleted to free up the memory space for registering data of the new endoscope.

Figure 12:
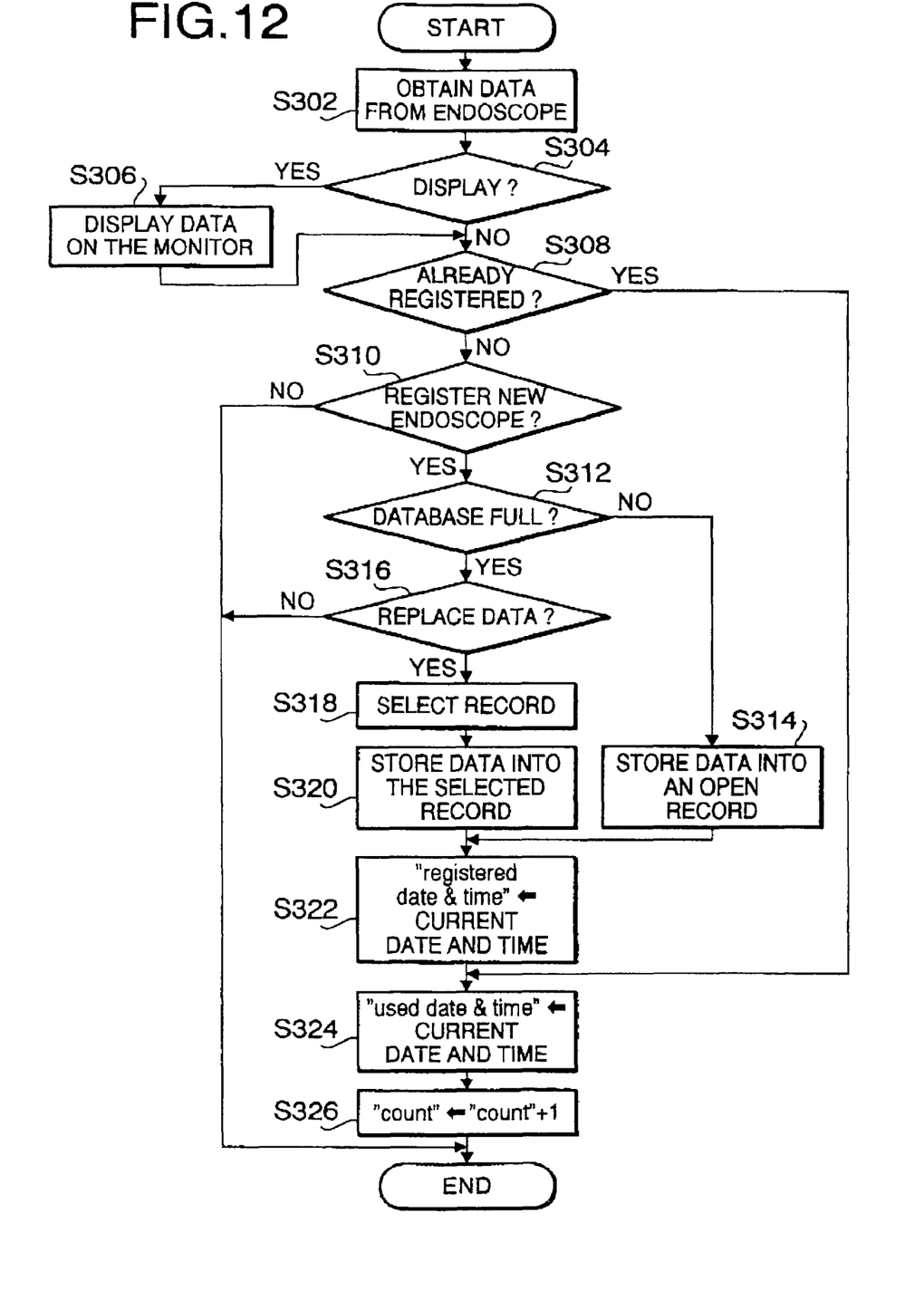
FIG. 12 is a flow chart showing the operation of the processor when the electronic endoscope is connected according to another embodiment of the invention.

FIG. 12 shows a flow chart of the operation of the processor 200 when the electronic endoscope is connected according to another embodiment of the invention.

In this embodiment, the processor 200 first obtains the data stored in the EEPROM 102 of the electronic endoscope 100 (S302). A part of or all of the data obtained are displayed on the monitor 300 if a predetermined command is inputted to the keyboard 400, operation panel 207, or the operation buttons 107 so that the operator can confirm the data of the electronic endoscope 100 (S304, S306).

Next, the processor 200 decides whether the currently connected electronic endoscope 100 is already registered with the database in the memory 208 by searching for a record including the "serial no." and "scope name" that matches those obtained from the electronic endoscope 100 (S308).

If there is a record including the same data (S308:Yes), which indicates the currently connected electronic endoscope 100 is already registered, then the operation of the processor 200 proceeds to S324 and S326 which will be described later.

If, however, there isn't any record including same data (S308:No), that is, the currently connected electronic endoscope 100 is a new one, the processor 200 displays a message asking the operator whether or not the new electronic endoscope 100 should be registered with the database, and accepts an instruction from the operator via the keyboard 400, the operation panel 207, or the operation buttons 107 (S310).

If the operator inputs an instruction not to register the new electronic endoscope 100e, the processor exits the present routine. If an instruction to register the new electronic endoscope 100 is inputted, then the processor 200 checks whether the database established in the memory 208 is full or not (S312). This is achieved by counting the number of endoscopes already registered with the database if the number is less than 39, which means the database is not yet full (S312:No), then the processor 200 stores the endoscope data obtained in S302 into an open record in the memory 208 (S314). Note that, in S314, the processor 200 may display the content of the database and let the operator select the open record into which the data should be stored.

In the case the database in the memory 208 is full (S312:Yes), that is, 39 endoscopes are already registered with the database, the processor 200 displays a message on the monitor asking whether the data of one of the registered endoscopes should be replaced with that of the new endoscope, and accepts an instruction from the operator via the keyboard 400, operation panel 207, or the operation button 107 (S316).

If an instruction not to replace data is accepted, the processor 200 exits the present routine without registering the new endoscope with the database (S316:No).

If an instruction to replace data is accepted (S316:YES), then the processor 200 displays the content of the database in the memory 208 on the monitor 300 and lets the operator select the record, or the registered endoscope, of which data should be replaced (S318) Thus, the operator can select the endoscope to be canceled by comparing the data, such as "ownership", "spec", and "expiration", of each registered endoscope and inputting the register number of one from the keyboard 400, for example.

Next, the processor 200 deletes the data in the record corresponding to the register number inputted, except the register number itself, and stores the data obtained from the EEPROM 102 of the electronic endoscope 100 (S320).

After performing S314 or S320, the processor 200 stores the current date and time outputted from the RTC 209 into the "registered date & time" of the record into which the processor 200 has Just stored the data in S314 or S320 (S322).

The processor 200 also set the current date and time obtained from the RTC 209 into the "used data & time" of the record which includes the data of the currently connected endoscope 100 (S324). Further, the processor 200 increments "count" of the same record (S326) and exits the present routine.

Figure 13:
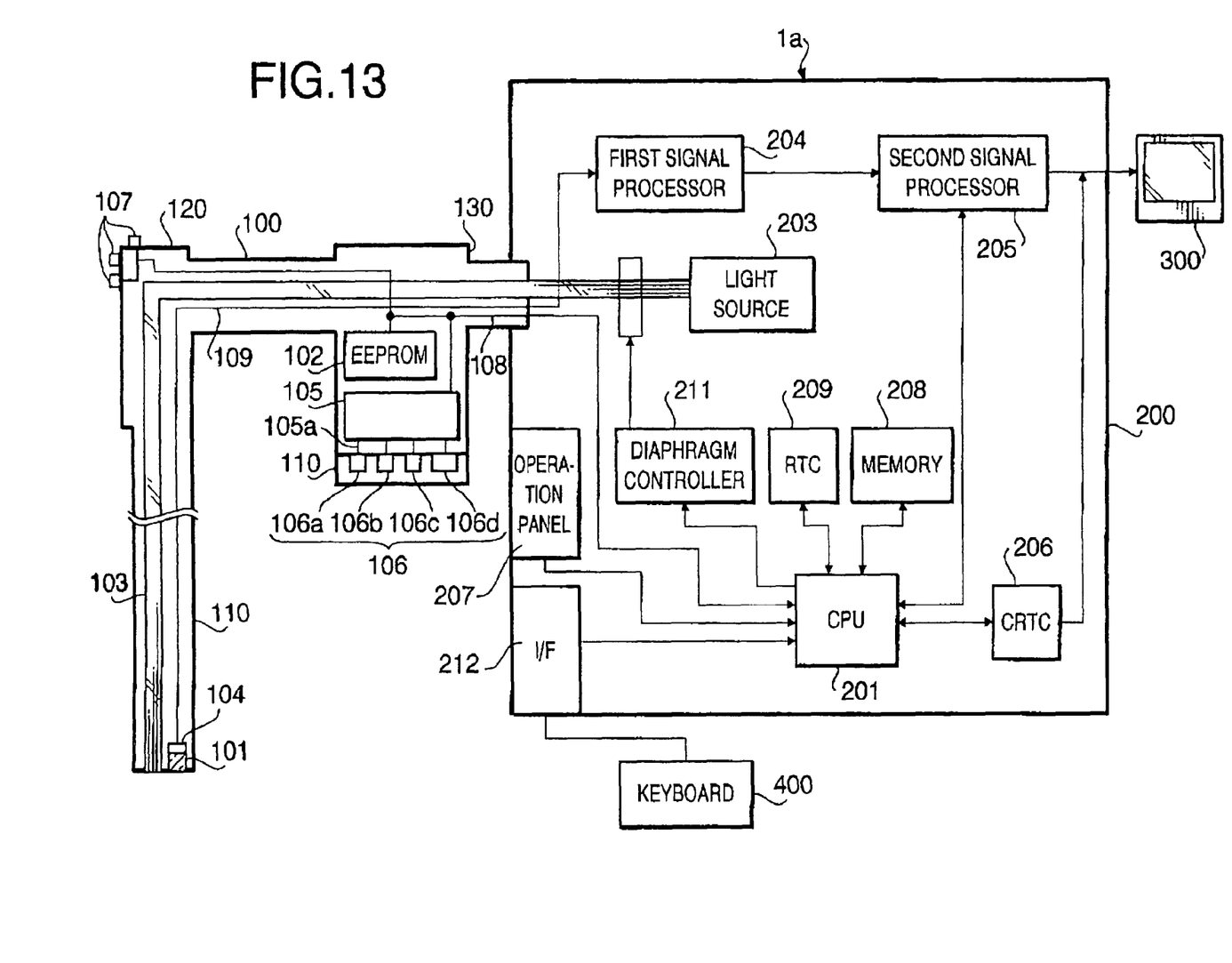
FIG. 13 schematically shows a modified configuration of the electronic endoscope system of FIG. 1.

FIG. 13 schematically shows a modified configuration of the electronic endoscope system 1 of FIG. 1. Note that the electronic endoscope system of FIG. 13 is essentially same as the system of FIG. 1 except the points described hereinafter.

The modified electronic endoscope system 1a of FIG. 13 has a switch device 106 which is provided to the connector 130 of the endoscope 100. The switch device 106 is configured to memorize, by its state, a part of the information that is stored in the EEPROM 102 in the electronic endoscope system 1 of FIG. 1. In the present case, the switch device 106 memorizes information related to the ownership, the specifications and the expiration of the endoscope 100. Other information on the endoscope 100 that are recited in FIG. 2 are stored in the EEPROM 102 as in the system of FIG. 1. The processor 200 obtains the information of the endoscope 100 partly from the EEPROM 102 and partly from the switch device 106, by checking the state of the switch device 106, and stores those data into the memory 208 if the endoscope 100 is a new one.

The switch device 106 includes four switch elements 106a, 106b and 106c such as dip switches each having ON and OFF states. However, two or more rotary switches having many states may also be used for switch elements 106a, 106b and 106c instead of dip switches.

The state of first and second switch elements 106a and 106b represents information related to the ownership of the endoscope 100. For example, if the states of first and second switch elements 106a and 106b are both OFF, it indicates the endoscope is a purchased one. If the first switch element 106a is OFF while the second switch element 106b is ON, the endoscope 100 is leased for a long term. Further, if the first switch element 106a is ON while the second switch element 106b is OFF, the endoscope 100 is leased for a short term.

The state of the third switch element 106c indicates the specifications of the endoscope That is, the third switch element 106*c* is set ON for the endoscope 100 of standard specifications, and OFF for the endoscope 100 having special specifications.

The switch device 106 further includes a fourth switch element 106*d* for setting the expiration date of the lease of the endoscope. The fourth switch element 106*d* may be a rotary switch by which the date month and year of expiration can be set up.

The switch device 106 further includes a switch state detector 105 which is connected to each of the switch elements 106*a*, 106*b*, 106*c* and 106*d* via a cable 105*a*. The switch state detector 105 generates signals corresponding to the states of the switch elements and outputs it to the CPU 201 via the signal cable 108.

A watertight cover member 110 is also provided detachably to the connector 130 to prevent the switch elements 106*a*–106*d* from being operated unintentionally.

It should be noted that the switch state detector 105 may be replaced with a plurality of I/O ports, each connected to different one of the switch elements 106*a*–106*d*. In this case, the CPU 201 itself detects the state of each switch elements 106*a*–106*d* via the I/O ports to obtain information related to the ownership, the specifications and the expiration of the endoscope 100.

It should be also noted that the switch device 106 may be provided to the operation portion 120 of the endoscope 100 instead of to the connector 130.

The present disclosure relates to the subject matters contained in Japanese Patent Application No. P2001-206644, filed on Jul. 6, 2001, and Japanese Patent Application No. P2001-263445, filed on Aug. 31, 2001, which are expressly incorporated herein by reference in their entireties.

What is claimed is:

1. An endoscope system comprising:
   a processor configured to be selectively physically connected to each of a plurality of different endoscopes, the processor receiving and processing signals from an endoscope that is selectively physically connected to said processor, the processor including a database that stores a plurality of pieces of endoscope data each corresponding to a different endoscope, each piece of said endoscope data being associated with ownership information, said ownership information indicating a term for which said corresponding endoscope is allowed to be utilized; and
   a database managing device that selects one piece of said plurality of pieces of endoscope data stored in said database and replaces said selected piece of endoscope data with a new piece of endoscope data corresponding to a new endoscope, said database managing device selecting said piece of endoscope data to be replaced based on said ownership information.

2. The endoscope system according to claim 1, wherein said ownership information includes information on whether the corresponding endoscope is purchased, and wherein said database managing device selects said piece of endoscope data related to the endoscope not being purchased in preference to other pieces of endoscope data.

3. The endoscope system according to claim 1, wherein said ownership information includes information on whether the corresponding endoscope is leased, and wherein said database managing device selects said piece of endoscope data related to the endoscope being leased in preference to other pieces of endoscope data.

4. The endoscope system according to claim 3, wherein said ownership information includes information on whether a term of lease of the endoscope is less than a predetermined period, and wherein said database managing device selects said endoscope data related to the term of lease less than the predetermined period in preference to other pieces of endoscope data.

5. The endoscope-system according to claim 3, wherein said ownership information includes information on a term of lease of the endoscope, and wherein said database managing device selects said piece of endoscope data based on the term of lease having expired.

6. The endoscope system according to claim 1, wherein each of said plurality of pieces of endoscope data is associated with registration information including a date of said plurality of pieces of endoscope data being stored into said database, and wherein said database managing device selects said piece of endoscope data to be replaced based on said registration information from among a plurality of pieces of said endoscope data pre-selected based on said ownership information.

7. The endoscope system according to claim 6, wherein said database managing device selects said piece of endoscope data related to said registration information including the oldest date.

8. The endoscope system according to claim 1, wherein each of said plurality of pieces of endoscope data is associated with used date information including a date when the corresponding endoscope was used for the last time, and wherein said database managing device selects said piece of endoscope data to be replaced based on said used date information from among a plurality of pieces of said endoscope data pre-selected based on said ownership information.

9. The endoscope system according to claim 8, wherein said database managing device selects said piece of said endoscope data based on said used date information including the oldest date.

10. An endoscope system comprising:
    a processor configured to be selectively physically connected to each of a plurality of different endoscopes, the processor receiving and processing signals from an endoscope that is selectively physically connected to said processor, the processor including a database that stores a plurality of pieces of endoscope data each corresponding to a different endoscope, each piece of said endoscope data being associated with term information, each piece of said term information indicating a term for which said piece of endoscope data is valid; and
    a database managing device that selectively deletes said piece of endoscope data in said database based on said term information.

11. The endoscope system according to claim 10, wherein said term information includes a term of lease of the corresponding endoscope.

12. The endoscope system according to claim 10, wherein said database managing device selectively deletes said endoscope data when said database does not have memory space for storing a piece of new endoscope data.

\* \* \* \* \*